United States Patent
Allen et al.

(10) Patent No.: US 11,083,837 B2
(45) Date of Patent: Aug. 10, 2021

(54) SECURE MEDICATION DELIVERY

(71) Applicant: International Business Machines Corporation, Armonk, NY (US)

(72) Inventors: Ira L. Allen, Dallas, TX (US); Gregory J. Boss, Saginaw, MI (US); Lawrence A. Clevenger, Rhinebeck, NY (US); Andrew R. Jones, Round Rock, TX (US); Kevin C. McConnell, Austin, TX (US); John E. Moore, Jr., Brownsburg, IN (US)

(73) Assignee: International Business Machines Corporation, Armonk, NY (US)

( * ) Notice: Subject to any disclaimer, the term of this patent is extended or adjusted under 35 U.S.C. 154(b) by 251 days.

(21) Appl. No.: 15/076,975

(22) Filed: Mar. 22, 2016

(65) Prior Publication Data

US 2017/0274139 A1   Sep. 28, 2017

(51) Int. Cl.
| | |
|---|---|
| *A61M 5/14* | (2006.01) |
| *A61M 5/162* | (2006.01) |
| *G16H 20/10* | (2018.01) |
| *G07F 17/00* | (2006.01) |
| *A61M 31/00* | (2006.01) |

(52) U.S. Cl.
CPC .............. *A61M 5/14* (2013.01); *A61M 5/162* (2013.01); *G07F 17/0092* (2013.01); *G16H 20/10* (2018.01); *A61M 31/002* (2013.01)

(58) Field of Classification Search
CPC ........... B81C 1/00071; B81B 2203/04; B81B 2201/085; B81B 2201/058; A61M 31/002; A61M 2205/04; A61M 5/14; A61M 5/162; G06F 19/3468; G06F 19/346; A61B 5/0088; A61B 17/1626; A61B 2017/00022; A61B 2018/00636; G16H 20/10; G07F 17/0092
See application file for complete search history.

(56) References Cited

U.S. PATENT DOCUMENTS

| | | |
|---|---|---|
| 2,769,443 A | 11/1956 | Dunmire |
| 5,700,998 A | 12/1997 | Palti |
| (Continued) | | |

FOREIGN PATENT DOCUMENTS

EP        1973593 B1     4/2013

OTHER PUBLICATIONS

Allen et al., "Secure Medication Delivery", U.S. Appl. No. 15/076,801, filed Mar. 22, 2016, 40 pages.

(Continued)

*Primary Examiner* — Lauren P Farrar
*Assistant Examiner* — Hamza A Darb
(74) *Attorney, Agent, or Firm* — Stephen R. Yoder (57) ABSTRACT

A method includes providing a medication delivery vehicle comprising a reservoir with a seal formed thereon and a cantilevered beam micro-machined from a layer of material and coupled to the reservoir, the cantilevered beam comprising a tip for puncturing the seal, applying an electric field to the cantilevered beam that impels the tip forward and causes the tip to break through the seal of the reservoir, and changing the electric field to impel the micro-machined tip backward and thereby release a medication from the reservoir. A computer program product and computer system corresponding to the method are also disclosed.

20 Claims, 11 Drawing Sheets

(56) References Cited

U.S. PATENT DOCUMENTS

| | | | |
|---|---|---|---|
| 5,853,101 | A | 12/1998 | Weinstein |
| 6,557,740 | B1 | 5/2003 | Dent |
| 6,833,112 | B2 | 12/2004 | Hoummady |
| 6,875,208 | B2 * | 4/2005 | Santini, Jr. ............ A61K 9/0009 604/890.1 |
| 6,985,870 | B2 | 1/2006 | Martucci et al. |
| 7,175,044 | B2 | 2/2007 | Benktzon |
| 7,916,282 | B2 | 3/2011 | Duineveld |
| 8,219,413 | B2 | 7/2012 | Martinez et al. |
| 8,548,623 | B2 | 10/2013 | Poutiatine et al. |
| 8,616,393 | B2 | 12/2013 | Vessa |
| 2004/0073175 | A1 | 4/2004 | Jacobson |
| 2004/0158350 | A1 | 8/2004 | Ostergaard |
| 2004/0193325 | A1 | 9/2004 | Bonderud |
| 2005/0206483 | A1 | 9/2005 | Pashby |
| 2006/0265246 | A1 | 11/2006 | Hoag |
| 2007/0151989 | A1 * | 7/2007 | Espinosa ............ B81C 1/00111 222/462 |
| 2007/0186923 | A1 | 8/2007 | Poutiatine |
| 2009/0043253 | A1 | 2/2009 | Podaima |
| 2009/0321295 | A1 | 12/2009 | Ede |
| 2010/0089790 | A1 | 4/2010 | Wiggins |
| 2010/0105735 | A1 | 4/2010 | Palmer |
| 2010/0129512 | A1 | 5/2010 | Accursi |
| 2010/0171596 | A1 * | 7/2010 | Burke ............ G06K 19/07749 340/10.4 |
| 2011/0098674 | A1 | 4/2011 | Vicente |
| 2012/0101446 | A1 | 4/2012 | Heald |
| 2013/0238119 | A1 | 9/2013 | Simmons |
| 2014/0099594 | A1 * | 4/2014 | Li ............ G06F 19/00 433/27 |
| 2014/0163664 | A1 | 6/2014 | Goldsmith |
| 2014/0207014 | A1 | 7/2014 | Roxhed |
| 2014/0285314 | A1 | 9/2014 | Muecke et al. |
| 2015/0343144 | A1 | 12/2015 | Altschul |
| 2015/0359711 | A1 | 12/2015 | Ducatt |
| 2016/0029963 | A1 | 2/2016 | Hyde |
| 2018/0307798 | A1 | 10/2018 | Allen |

OTHER PUBLICATIONS

Allen et al., "Secure Medication Delivery", U.S. Appl. No. 15/076,900, filed Mar. 22, 2016, 40 pages.

Allen et al., "Secure Medication Delivery", U.S. Appl. No. 15/076,941, filed Mar. 22, 2016, 40 pages.

IBM Appendix P, list of IBM Patents or patent applications treated as related, Mar. 22, 2016, 2 pages.

Gates, Sara, "Passwords In Tattoos And Pills? Motorola Announces Plans For Wearable Tech (Video)", The Huffington Post, Posted: Jun. 3, 2013, 2 pages, <http://www.huffingtonpost.com/2013/06/03/passwords-tattoos-pills-motorola_n_3378767.html>.

Lu et al., "MEMS-Based Inductively Coupled RFID Transponder for Implantable Wireless Sensor Applications", IEEE Transactions on Magnetics, vol. 43, No. 6, June 2007, © 2007 IEEE, 3 pages.

Robarts, Stu, "FDA approves PillCam video camera that you swallow", gizmag, Health and Wellbeing, Feb. 6, 2014, © Gizmag 2003—2016, 8 pages, <http://www.gizmag.com/fda-approval-pillcam-colon/30740/>.

"Enteric Coating", From Wikipedia, the free encyclopedia, This page last modified on Dec. 10, 2015, 2 pages, <https://en.wikipedia.org/wiki/Enteric_coating>.

"Osmotic controlled-release oral delivery system", From Wikipedia, the free encyclopedia, This page was last modified on Jun. 30, 2015, 1 page, <https://en.wikipedia.org/wiki/Osmotic_controlled-release_oral_delivery_system>.

"Proteus Digital Health", Proteus Digital Health, Inc., 2600 Bridge Parkway, Redwood City, CA 94065, © 2016 All Rights Reserved Proteus Digital Health, printed on Jan. 8, 2016, 4 page, <http://www.proteus.com/>.

"Resources: health care", Publication title: New Hampshire Business Review, Publication date: Oct. 26, 2007 Publisher: Business Publications, Inc., ISSN: 0164-8152, Copyright: Copyright 2007 Gale, Cengage Learning, 4 pages.

"Inert." Merriam-Webster.com. Retrieved Jul. 27, 2018, 15 pages.

"Inert." Wiktionary. Retrieved Jul. 27, 2018, 3 pages.

* cited by examiner

SECURE MEDICATION DELIVERY

BACKGROUND OF THE INVENTION

The present invention relates generally to the field of medication delivery, and more specifically to ensuring a patient receives the proper medication.

As the utilization of pharmaceuticals in medicine has drastically increased in recent years, the incidence of improper administration of pharmaceuticals has also increased. Patients who are prescribed a medication largely rely on the pharmacist or other medication provider to ensure they are receiving the correct prescribed medication. In cases where a medication provider makes a mistake, or may be otherwise motivated to provide a different medication than has been prescribed, a patient may be provided an incorrect medication that could potentially be unsafe for that patient.

SUMMARY

As disclosed herein, a method includes providing a medication delivery vehicle comprising a reservoir with a seal formed thereon and a cantilevered beam micro-machined from a layer of material and coupled to the reservoir, the cantilevered beam comprising a tip for puncturing the seal, applying an electric field to the cantilevered beam that impels the tip forward and causes the tip to break through the seal of the reservoir, and changing the electric field to impel the micro-machined tip backward and thereby release a medication from the reservoir. A computer program product and computer system corresponding to the method are also disclosed.

DETAILED DESCRIPTION

Some currently available techniques for enabling a patient to confirm he or she is receiving the appropriate medication rely on the patient's willingness to (and ability to) compare a received medication to a picture or depiction of the appropriate medication. For example, there are published and web based reference sheets where a medication can be looked up and an image of the medication is provided showing the shape, color, and markings of the appropriate pill. Carefully comparing medications to these reference sheets can be time consuming, and sometimes a patient may note that the pill looks similar and not think much more about it. Additionally, some patients may be easily convinced that a different looking medication is just a newer version of the appropriate medication. The embodiments disclosed herein provide enhanced security measures to ensure a patient is receiving the appropriate medication without requiring that the patient have any knowledge of the medication.

Figure 1:
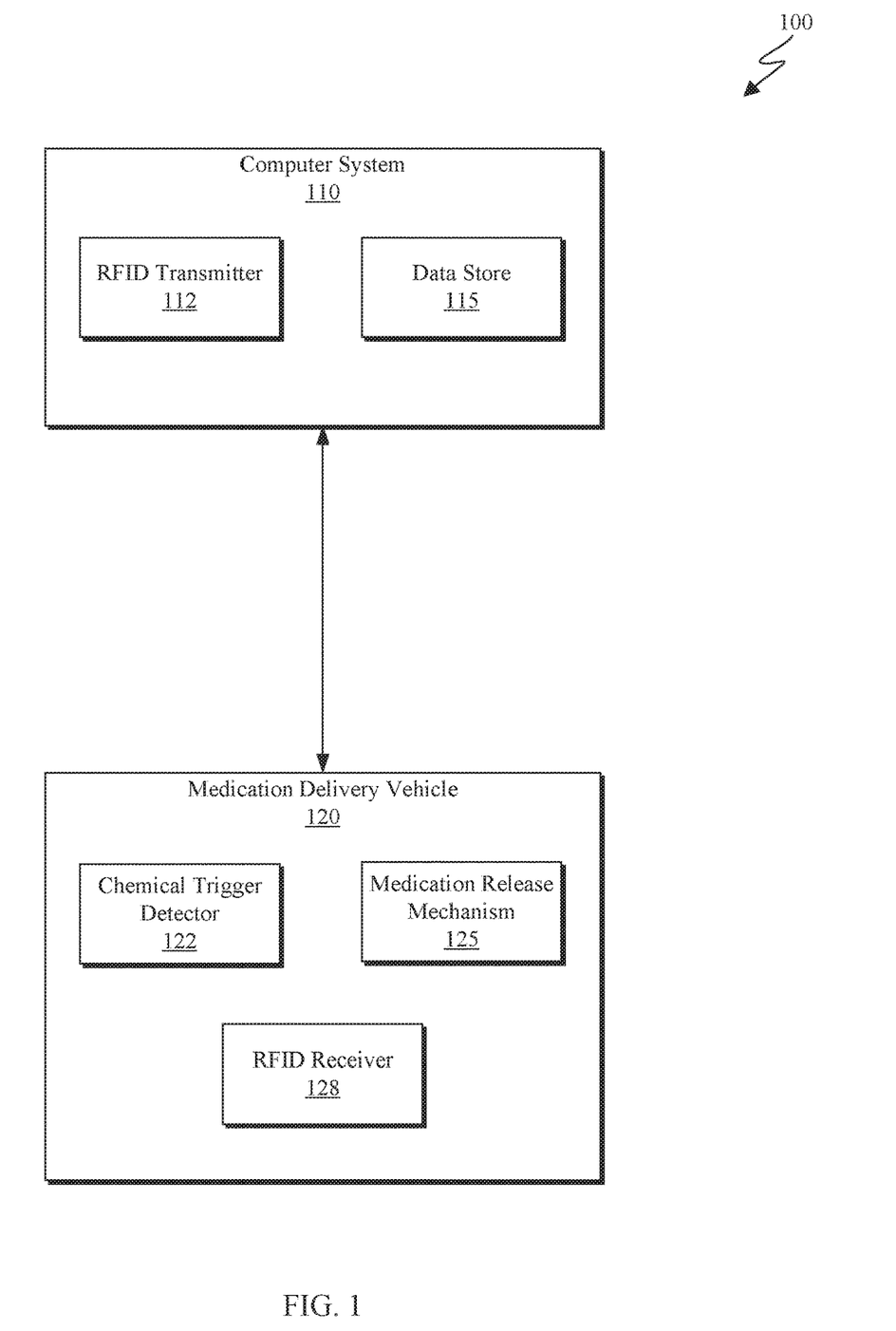
FIG. 1 is a block diagram depicting one example of a medication delivery system in accordance with at least one embodiment of the present invention.

FIG. 1 is a block diagram depicting one example of a medication delivery system 100 in accordance with at least one embodiment of the present invention. As depicted, medication delivery system 100 includes computer 110 and medication delivery vehicle 120. Medication delivery system 100 may correspond to an environment in which the medication delivery methods disclosed herein may be executed to avoid improper medication administration.

Computer 110 can be a desktop computer, a laptop computer, a specialized computer server, or any other computer device known in the art. In some embodiments, computer 110 represents a computer system utilizing clustered computers and components to act as a single pool of seamless resources. In general, computer 110 is representative of any electronic device, or combination of electronic devices, capable of executing machine-readable program instructions, as described in greater detail with regard to FIG. 8. In at least one embodiment, computer 110 corresponds to a wearable computer worn by a patient.

As depicted, computer 110 includes a radio-frequency identification (RFID) transmitter 112 and a data store 115. RFID transmitter 112 may be configured to transmit a public key corresponding to a patient. The public key may be a marker unique to the patient. In at least one embodiment, the public key corresponds to markers within the patient's saliva. RFID transmitter 112 may be configured to provide a public key to a receiver on a medication delivery vehicle such as medication delivery vehicle 120. The RFID transmitter 112 may additionally be configured to receive the public key from a data store such as data store 115.

Data store 115 may be configured to store the public key as mentioned previously. Data store 115 may be any non-volatile storage media known in the art. For example, data store 115 can be implemented with a tape library, optical library, one or more independent hard disk drives, or multiple hard disk drives in a redundant array of independent disks (RAID). Similarly, data on data store 115 may conform to any suitable storage architecture known in the art, such as a file, a relational database, an object-oriented database, and/or one or more tables.

Medication delivery vehicle 120 may be configured to release a medication into a patient. As depicted, the medication delivery vehicle 120 includes a chemical trigger detector 122, a medication release mechanism 125, and an RFID receiver 128. Details regarding multiple embodiments of how medication delivery vehicle 120 may operate are discussed with respect to FIG. 3 and FIG. 4. Details regarding how medication delivery vehicle 120 may be fabricated are discussed with respect to FIG. 5 and FIGS. 7A-7L.

Chemical trigger detector 122 may be a sensor configured to detect the presence of a chemical trigger within a patient. In some embodiments, the chemical trigger corresponds to a chemical managed by the medication delivered by medication delivery vehicle 120. For example, if a patient is taking a medication to manage an iron deficiency, the chemical trigger detector 122 may be configured to detect and measure the patient's iron levels or a chemical corresponding thereto. In some embodiments, the chemical trigger detector 122 is configured to send a signal to medication release mechanism 125 if the iron level is found to be lower than a selected amount (e.g., to indicate that the patient needs a dose of medication).

RFID receiver 128 may be configured to receive an RFID signal indicating a public key, such as the RFID signal provided by RFID transmitter 112. RFID receiver 128 may be further configured to compare the received public key to a private key embedded in the MDV 120. In at least one embodiment, RFID receiver 128 is additionally configured to provide an indication of whether or not the public key and the private key match to medication release mechanism 125.

Figure 2:
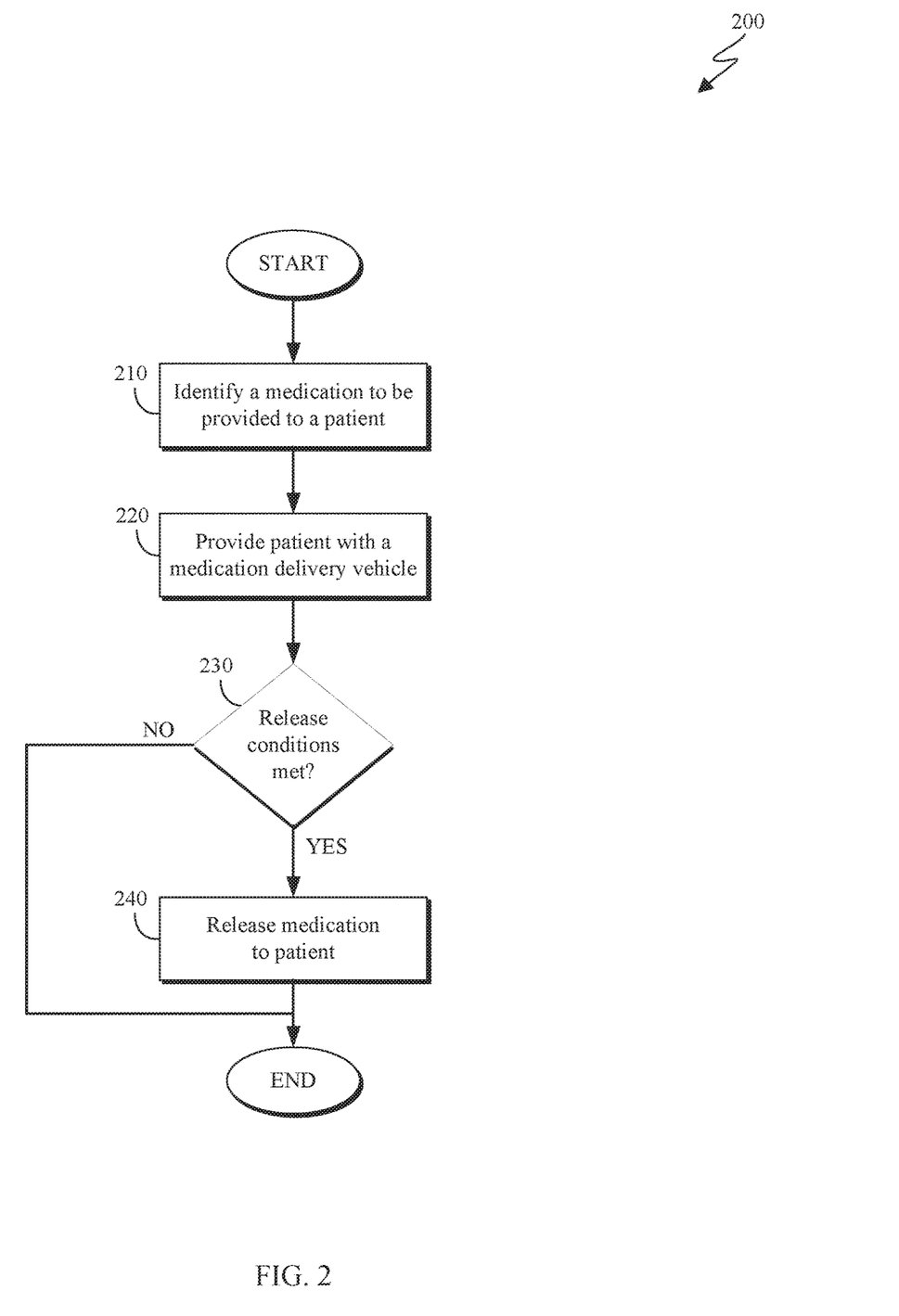
FIG. 2 is a flowchart depicting one example of a medication delivery management method in accordance with at least one embodiment of the present invention.

FIG. 2 is a flowchart depicting one example of a medication management method 200 in accordance with at least one embodiment of the present invention. As depicted, the medication delivery management method 200 includes identifying (210) an appropriate medication to be provided to a patient, providing (220) the patient with a medication delivery vehicle (MDV), determining (230) if a set of medication release conditions are met, and releasing (240) a medication to the patient. Medication management method 200 may be used to avoid exposing a patient to an incorrect medication.

Identifying (210) an appropriate medication to be provided to a patient may include receiving patient information corresponding to the patient from a medical authority. In one embodiment, the patient information is received from a medical provider such as a hospital or a doctor's office. The patient information may include a medical condition corresponding to the patient, as well as a medication to treat said medical condition. In embodiments where the patient information does not include an indication of a suggested medication, identifying (210) an appropriate medication may include searching a database of medications for a medication capable of treating the patient's medical condition.

Providing (220) the patient with a medication delivery vehicle (MDV) may include providing the patient with an ingestible medication delivery vehicle containing the identified appropriate medication. In some embodiments, the MDV is equipped with an RFID receiver configured to receive an RFID transmission of a public key. The MDV may also be equipped with a data store configured to store a private key corresponding to the patient. In at least some embodiments, the MDV is additionally equipped with a chemical trigger detector configured to determine a chemical trigger level within the patient. In said embodiments, the chemical trigger detector may be configured to compare the detected chemical trigger level to a selected chemical trigger level. The selected chemical trigger level may be a predetermined value that indicates the patient requires a dose of the medication stored within the MDV.

Determining (230) if a set of medication release conditions are met may include comparing the public key received via RFID transmission to the stored private key. If the public key and the private key do not match, then the set of medication release conditions are not met (230, no branch), and the medication remains unreleased. In some embodiments, determining (230) if a set of medication release conditions are met additionally includes determining if a detected chemical trigger level is below a selected chemical trigger level. If the detected chemical trigger level is not below the selected chemical trigger level, then the set of medication release conditions are not met (230, no branch), and the medication remains unreleased. If all medication release conditions are met (230, yes branch), then the method continues by releasing (240) the medication to the patient.

Releasing (240) a medication to the patient may include activating the medication delivery vehicle to release stored medication into the patient. Specific mechanisms for releasing medication to the patient are discussed with respect to FIGS. 5 and 6. In some embodiments, where a MDV is configured to provide multiple doses of a medication over a period of time, releasing (240) a medication to the patient may further include providing a notification to the patient if the MDV is out of medication to release.

Figure 3:
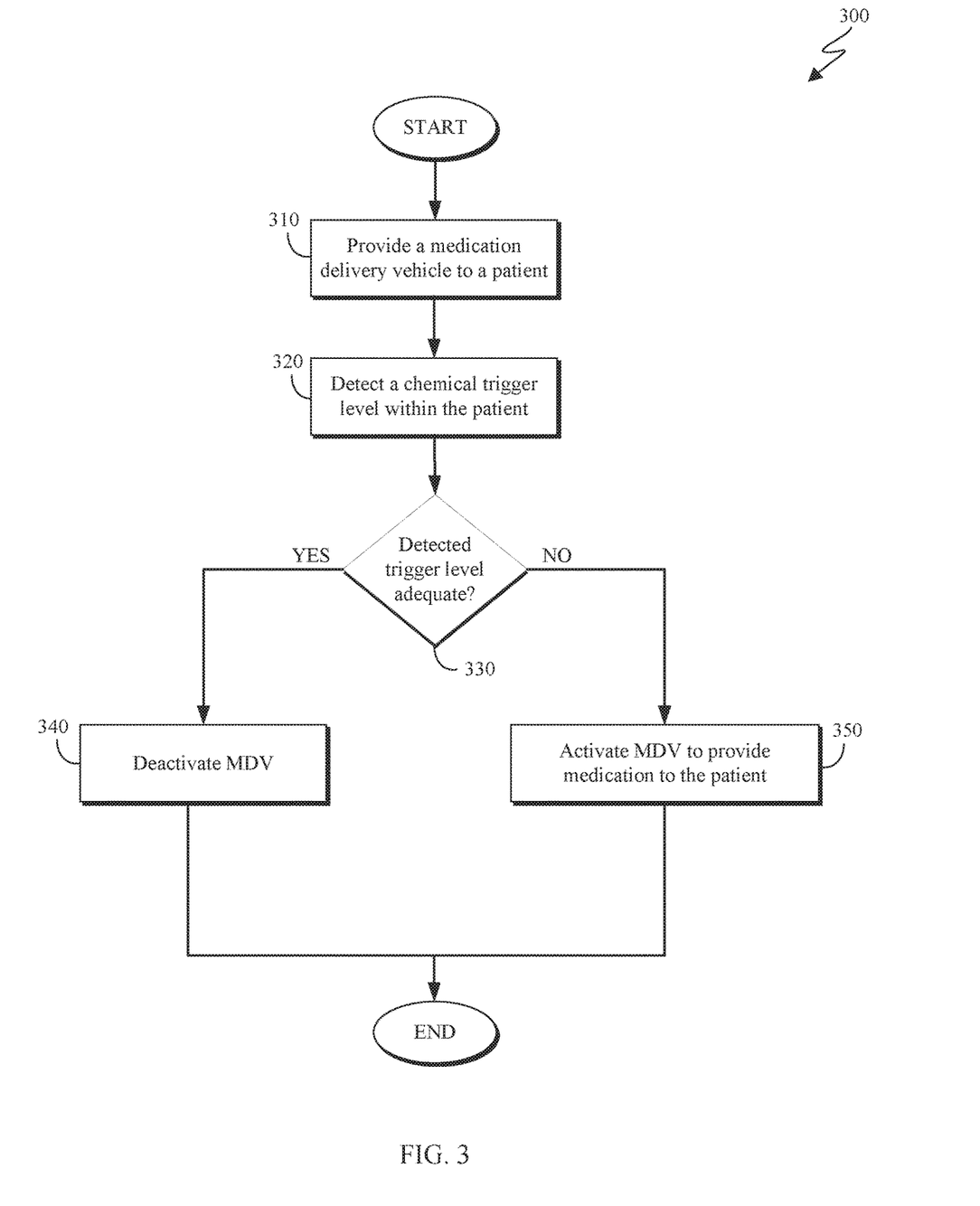
FIG. 3 is a flowchart depicting one example of a medication delivery method in accordance with at least one embodiment of the present invention.

FIG. 3 is a flowchart depicting one example of a medication delivery method 300 in accordance with at least one embodiment of the present invention. As depicted, medication delivery method 300 includes providing (310) a medication delivery vehicle (MDV) to a patient, detecting (320) a chemical trigger level within the patient, determining (330) whether the detected chemical trigger level is less than a selected trigger level, deactivating (340) the medication delivery vehicle, and activating (350) the medication delivery vehicle to provide medication to the patient. Medication delivery method 300 may ensure a medication is only released to the appropriate patient to whom it was prescribed.

Providing (310) a medication delivery vehicle (MDV) to a patient may include providing an ingestible MDV to a patient. In one or more embodiments, the MDV comprises a reservoir (e.g., a sealed cavity) containing an appropriate medication to be released within the patient. The MDV may additionally comprise a chemical trigger detector configured to detect a chemical trigger level within the patient. In some embodiments, the MDV is additionally configured to provide the detected chemical trigger level to a computer system. The provided MDV may also be configured to release the appropriate medication into the patient when activated. In one or more embodiments, the MDV is equipped with a secondary security measure configured to render the medication inert.

Detecting (320) a chemical trigger level within the patient may include receiving an indication of the chemical trigger level from the provided MDV. In some embodiments, the chemical trigger corresponds to a chemical which is managed by the medication contained within the MDV. For example, if a patient is taking an MDV configured to provide an iron supplement, the MDV may be configured to detect an iron level within the patient. The detected chemical trigger level may be provided to a comparator module.

Determining (330) whether the detected chemical trigger level is adequate may include receiving a selected trigger level corresponding to the chemical trigger. The selected trigger level may also include an indication of whether the detected chemical trigger level must be above or below the selected trigger level to be deemed adequate. The received selected trigger level may be provided to a comparator module, along with the detected chemical trigger level, to determine whether the detected chemical trigger level is adequate. If the detected chemical trigger level is found to be adequate (330, yes branch), the method continues by deactivating (340) the medication delivery vehicle. If the detected chemical trigger level is found to be inadequate (330, no branch), the method continues by activating (350) the medication delivery vehicle.

Deactivating (340) the medication delivery vehicle may include leaving the reservoir containing medication intact. This may also be referred to as leaving the MDV "locked".

In other embodiments, deactivating (340) the MDV comprises activating the secondary security measure configured to render the medication within the MDV inert. For example, the secondary security measure may be configured to release a compound into the medication reservoir configured to make the medication inert or non-toxic. In some embodiments, the secondary security measure releases water into the medication reservoir to dilute the medicine to a safe level.

Activating (350) the medication delivery vehicle to provide medication to the patient may include sending a signal to the MDV instructing the MDV to release the medication. Releasing the medication from the MDV may include puncturing a seal on the medication reservoir to release the stored medication into the patient. A detailed embodiment of how the MDV releases medication upon activation is described with respect to FIG. 7.

Figure 4:
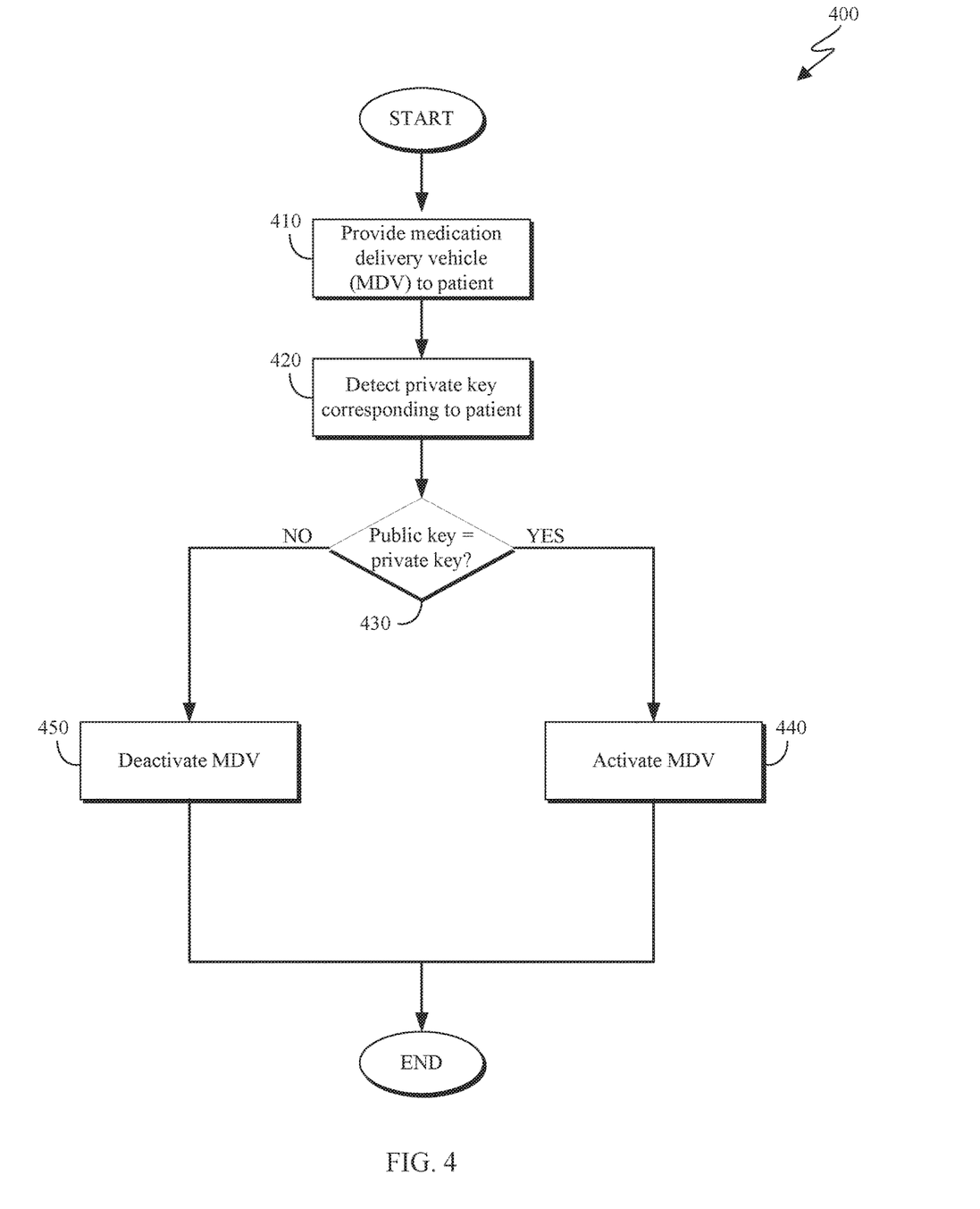
FIG. 4 is a flowchart depicting one example of a medication delivery method in accordance with at least one embodiment of the present invention.

FIG. 4 is a flowchart depicting one example of a medication release method 400 in accordance with at least one embodiment of the present invention. As depicted, medication release method 400 includes providing a medication delivery vehicle (MDV) to a patient, detecting (420) a private key corresponding to a patient, determining (430) if the private key matches a public key associated with the medication delivery vehicle, activating (440) the medication delivery vehicle, and deactivating (450) the medication delivery vehicle. Medication release method 400 may ensure a medication is not released into a patient unless it is a medication intended for the patient.

Providing a medication delivery vehicle (MDV) to a patient may include providing an ingestible MDV to a patient. In one or more embodiments, the MDV comprises a reservoir containing an appropriate medication to be released within the patient. The MDV may additionally comprise a radiofrequency identification (RFID) receiver configured to detect a private key corresponding to the patient. In some embodiments, the MDV additionally comprises a public key corresponding to the medication. The provided MDV may also be configured to release the appropriate medication into the patient when activated. In one or more embodiments, the MDV is equipped with a secondary security measure configured to render the medication inert.

Detecting (420) a private key corresponding to a patient may include identifying a private key provided via an RFID signal. In some embodiments, the private key is provided by a computer system corresponding to the patient. The computer system may be a wearable computer worn by the patient. The detected private key may be provided to a comparator module.

Determining (430) if the private key matches a public key associated with the medication delivery vehicle may include comparing the received private key to the public key stored in the MDV. The public key embedded in the MDV is selected to ensure that only the patient for whom the medication is intended will have a private key that matches the public key. If it is determined that the public key and the private key match (430, yes branch), then the method continues by activating (440) the medication delivery vehicle. If it is determined that the public key and the private key do not match (430, no branch), then the method continues by deactivating (450) the medication delivery vehicle.

Activating (440) the medication delivery vehicle to provide medication to the patient may include sending a signal to the MDV instructing the MDV to release the medication. Activating (440) the medication delivery vehicle occurs responsive to determining that the private key and public key match. Releasing the medication from the MDV may include puncturing the medication reservoir to release the stored medication into the patient. A detailed embodiment of how the MDV releases medication upon activation is described with respect to FIG. 7.

Deactivating (450) the medication delivery vehicle may include leaving the reservoir containing medication intact. This may also be referred to as leaving the MDV "locked". In other embodiments, deactivating (450) the MDV comprises activating the secondary security measure configured to render the medication within the MDV inert. For example, the secondary security measure may be configured to release a compound into the medication reservoir configured to make the medication inert or non-toxic. In some embodiments, the secondary security measure releases water into the medication reservoir to dilute the medicine to a safe level.

Figure 5:
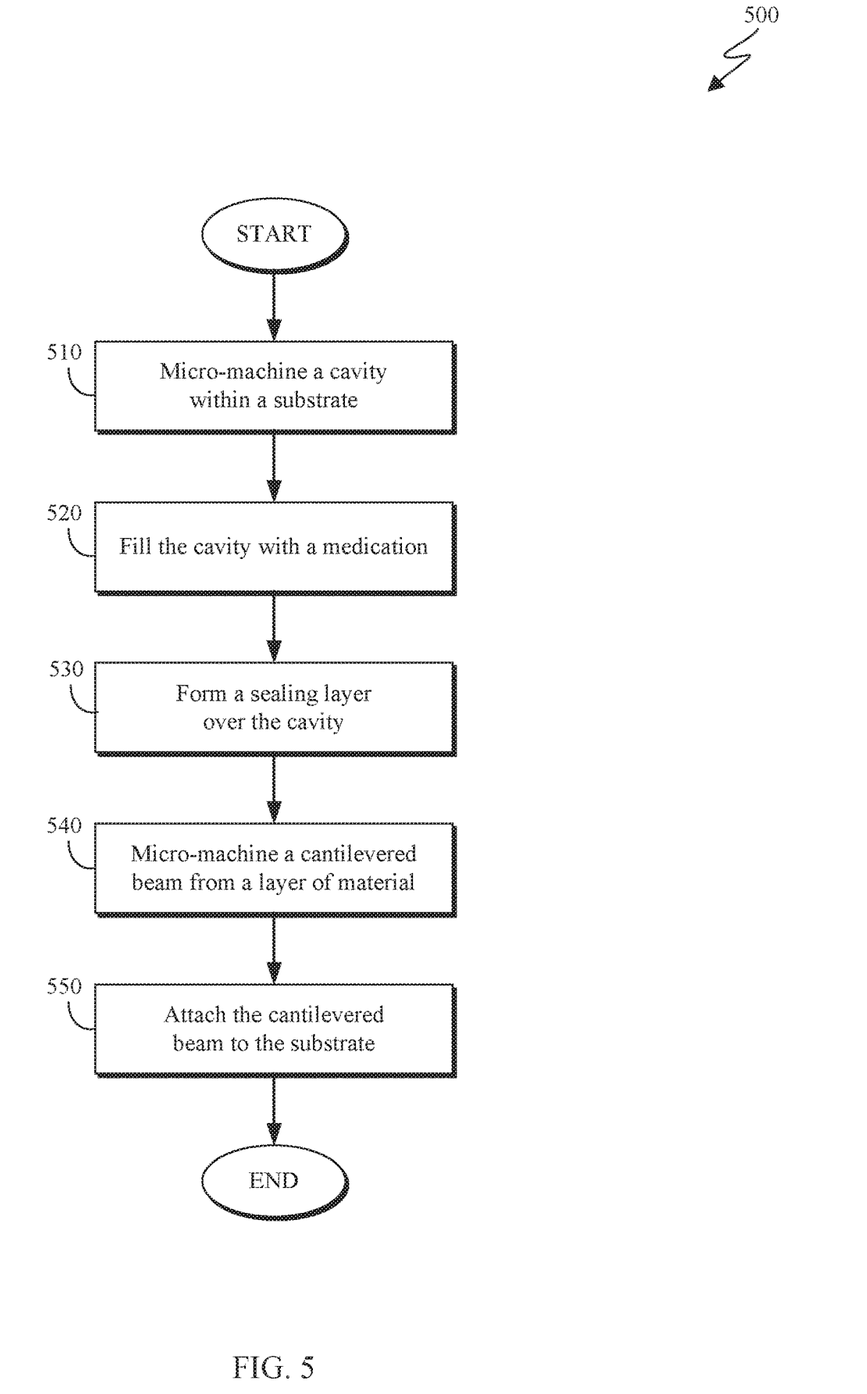
FIG. 5 is a flowchart depicting one example of a medication delivery vehicle fabrication method in accordance with at least one embodiment of the present invention.

FIG. 5 is a flowchart depicting one example of a medication delivery vehicle fabrication method in accordance with at least one embodiment of the present invention. As depicted, medication delivery vehicle fabrication method 500 includes micro-machining (510) a cavity within a substrate, filling (520) the cavity with a medication, forming (530) a sealing layer over the cavity, micro-machining (540) a cantilevered beam from a layer of material, and attaching (550) the cantilevered beam to the substrate. MDV fabrication method 500 may enable the production of a medication delivery vehicle configured to only release medication to an appropriate patient.

Micro-machining (510) a cavity within a substrate may include utilizing microelectromechanical systems (MEMS) fabrication techniques to create a cavity in a layer of substrate. In one embodiment, a chemical wet etching is used to create the cavity in the substrate. In other embodiments, dry etching is used to create the cavity in the substrate. The substrate in which the cavity is created may be selected according to a medication which will be stored in the cavity, Filling (520) the cavity with a medication may include depositing a medication into the micro-machined cavity. In some embodiments, the deposited medication is liquid medicine.

Forming (530) a sealing layer over the cavity may include depositing a layer of a sealing material over the top of the cavity to contain the medication. The sealing layer may be made of a material specifically selected to be permeable by a polysilicon tip. In one or more embodiments, the sealing layer corresponds to a base layer upon which a cantilevered beam is created. In certain embodiments, filling (520) the cavity and forming (530) the sealing layer over the cavity are jointly conducted operations. For example, a portion of the cavity may be sealed, and the cavity may be filled via the unsealed portion. Subsequently, the remaining portion of the sealing layer may be formed over the cavity.

Micro-machining (540) a cantilevered beam from a layer of material may comprise utilizing microelectromechanical systems (MEMS) fabrication techniques to manufacture a cantilevered beam. In one or more embodiments, the cantilevered beam is configured to puncture the sealing layer over the cavity to enable the medication in the cavity to be released. The MEMs may be configured to create a polysilicon tip on the cantilevered beam capable of puncturing the sealing layer. A step-by-step description of one embodiment of a polysilicon tip fabrication method is described with respect to FIGS. 7A-7G.

Attaching (550) the cantilevered beam to the substrate may include fixing one end of the cantilevered beam to the layer of substrate comprising the cavity filled with medication. In one or more embodiments, the cantilevered beam is fixed to the layer of substrate in a manner such that moving the cantilevered beam towards the layer of substrate will cause a polysilicon tip to puncture the seal layer over the cavity.

Figure 6:
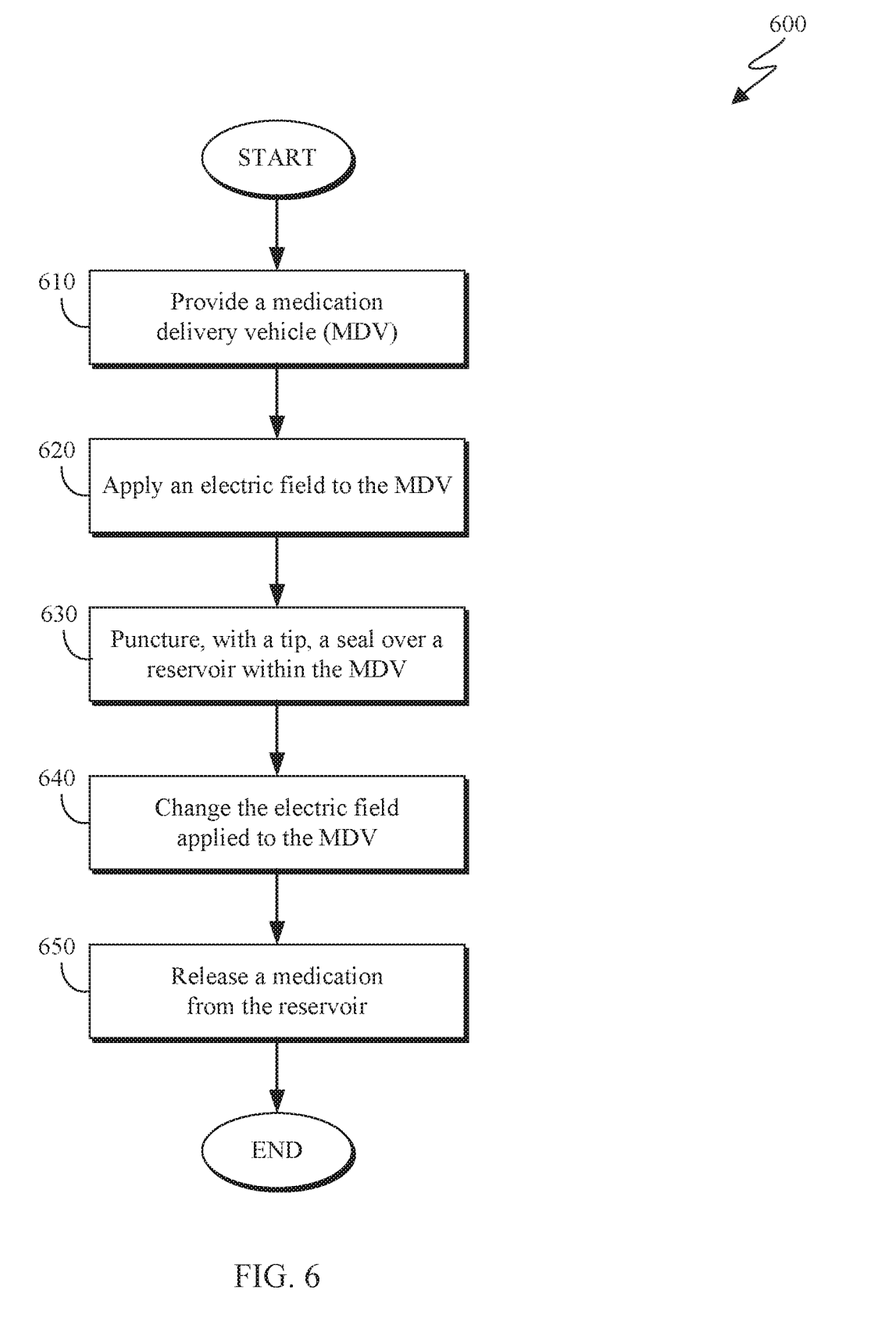
FIG. 6 is a flowchart depicting one example of a medication release method in accordance with at least one embodiment of the present invention.

FIG. 6 is a flowchart depicting one example of a polysilicon tip movement method 600. As depicted, the polysilicon tip movement method 600 includes providing (610) a medication delivery vehicle (MDV) to a patient, applying (620) an electric field to the MDV, puncturing (630), with a tip, a seal over a reservoir within the MDV, changing (640) the electric field applied to the MDV, and releasing (650) a medication from the reservoir. Medication release method 600 may enable medication to be released from a reservoir within an ingestible medication delivery vehicle inside a patient.

Providing (610) a medication delivery vehicle (MDV) to a patient may include providing an ingestible MDV to a patient. In one or more embodiments, the MDV comprises a reservoir or cavity with a sealing layer formed overtop. In one or more embodiments, the MDV comprises a cantilevered beam micro-machined from a layer of material and coupled to the reservoir. The cantilevered beam may comprise a polysilicon tip configured to puncture the sealing layer over the reservoir when activated. The polysilicon tip may be positioned such that moving it forward will puncture a sealing layer above the reservoir or cavity. In one or more embodiments, the MDV additionally comprise a radiofrequency identification (RFID) receiver.

Applying (620) an electric field to the MDV may include applying an electric field to the cantilevered beam within the MDV. The electric field may be applied in a manner such as to impel the cantilevered beam forward. In one or more embodiments, applying (620) an electric field to the MDV occurs responsive to receiving an RFID signal. The RFID signal, received by an RFID receiver, may be sent responsive to confirming one or more medication release conditions have been met. For example, the RFID signal may only be sent once it has been confirmed that a public key corresponding to the MDV matches a patient key corresponding to the patient. In additional embodiments, the RFID signal may only be sent once it has been confirmed that a detected chemical trigger level is inadequate.

Puncturing (630), with a tip, a seal over a reservoir within the MDV may include driving the polysilicon tip of the cantilevered beam through the sealing layer over the reservoir in the MDV. In one or more embodiments, the cantilevered beam is impelled forward by the applied electric field. In said embodiments, the polysilicon tip on the cantilevered beam is positioned in a manner such that when the cantilevered beam is impelled forward, the polysilicon tip punctures the sealing layer over the reservoir.

Changing (640) the electric field applied to the MDV may include altering the electric field applied to the MDV to impel the cantilevered beam in a different direction. In one embodiment, the electric field may be reversed to impel the cantilevered beam backwards, thus removing the polysilicon tip from the sealing layer and revealing a hole in the sealing layer over the reservoir. In other embodiments, changing (640) the electric field applied to the MDV includes removing the applied electric field and applying a second electric field in a manner such as to impel the cantilevered beam in a different direction.

Releasing (650) a medication from the reservoir may include impelling the cantilevered beam backwards so as to remove the polysilicon tip from the sealing layer. In one or more embodiments, the cantilevered beam is impelled backwards by the changed electric field. Removing the polysilicon tip from the sealing layer may leave a hole in the sealing layer through which the medication can escape into the patient.

Figure 7A:
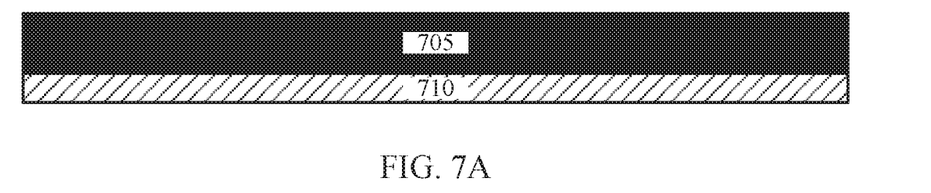
FIGS. 7A-7L depict steps of one embodiment of a medication delivery vehicle fabrication method in accordance with at least one embodiment of the present invention.

FIGS. 7A-7G depict steps of a polysilicon tip fabrication method in accordance with one embodiment of the present invention. FIG. 7A depicts a sealing layer 710 upon which a sacrificial layer 705 has been deposited. In one or more embodiments, sacrificial layer 705 is an oxide layer. The sealing layer 710 may correspond to a sealing layer deposited over a substrate layer comprising a medication reservoir (not pictured).

Figure 7B:
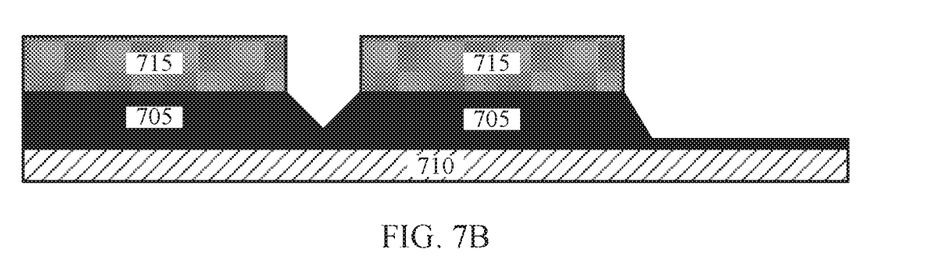
Figure 7C:
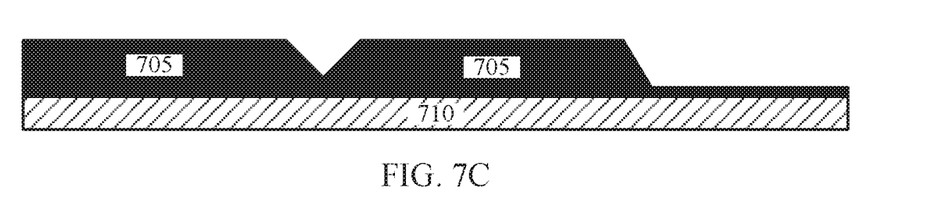

FIG. 7B depicts a photoresist layer 715 deposited on top of the sacrificial layer 705 and the sealing layer 710. Photoresist layer 715 may be a light-sensitive material used to form a patterned coating on sacrificial layer 705. In the depicted embodiment, the sacrificial layer has been etched with a polymerizing reactive ion etch to provide a tapered pattern in the sacrificial layer as depicted. Also depicted, the sacrificial layer has not been etched all the way down to the sealing layer. That is, there still remains at least a slim sacrificial layer across the entire sealing layer in the depicted embodiment. The photoresist layer 715 may be removed once the sacrificial layer 705 has been patterned as desired as shown in FIG. 7C. Specifically, FIG. 7C depicts a tapered pattern in sacrificial layer 705 created by the implementation of the photoresist layer.

Figure 7D:
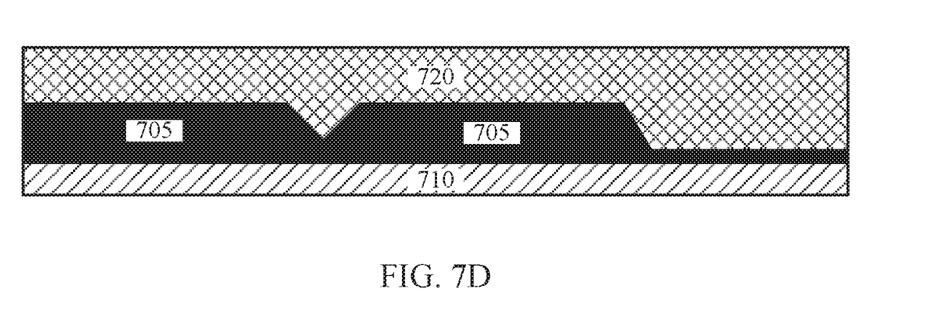
Figure 7E:
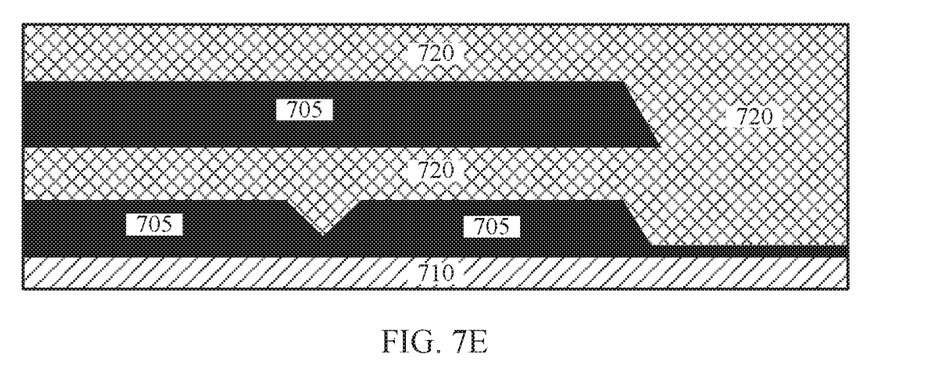

FIG. 7D depicts a polysilicon layer 720 deposited on top of the patterned sacrificial layer 705 and the sealing layer 710. As depicted, the polysilicon layer 720 is deposited over the entirety of the sacrificial layer 705, and fills the tapered pattern in the sacrificial layer as well. The polysilicon layer 720 may be deposited over the sacrificial layer using any number of methods known in the art, such as silane decomposition. The steps depicted in FIGS. 7A-7D may be repeated one or more times, to provide multiple sacrificial layers 705 and multiple polysilicon layers 720, as depicted in FIG. 7E. Notable with respect to FIG. 7E, there may be multiple sacrificial layers and multiple polysilicon layers corresponding to a single sealing layer.

Figure 7F:
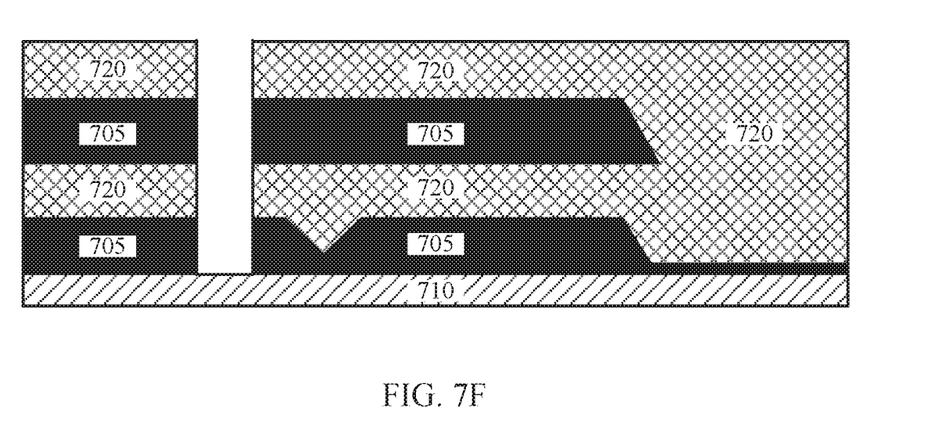

FIG. 7F depicts a stack comprising two sacrificial layers 705 and two polysilicon layers 720 deposited on a sealing layer 710. As depicted, the sacrificial layers 705 and polysilicon layers 720 have been patterned down to the sealing layer. Similar to the step discussed with respect to FIG. 7B, a polymerizing reactive ion etch may be used to pattern the stack. In the depicted embodiment, the sealing layer is not patterned.

Figure 7G:
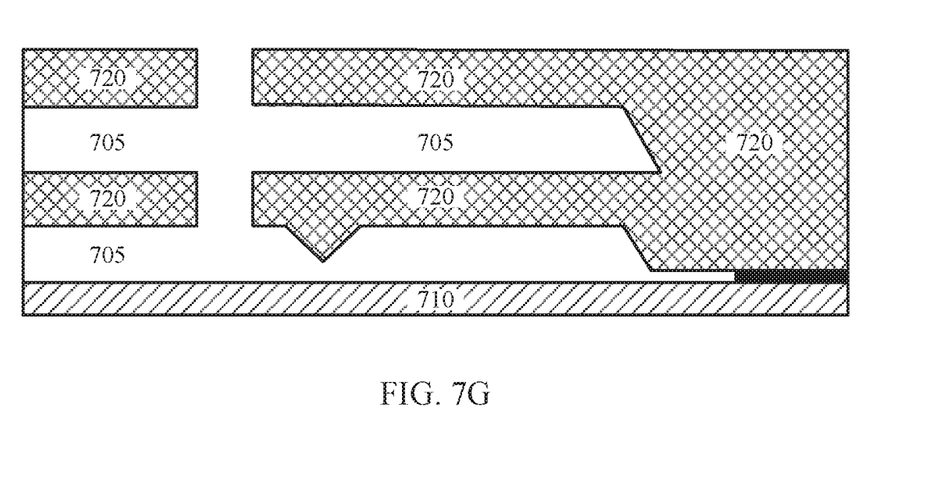

FIG. 7G depicts two polysilicon layers 720 deposited over a sealing layer 710. FIG. 7G depicts the same stack as FIG. 7F after the sacrificial layers have been removed. In one embodiment, the oxide is removed using a hydrofluoric acid wet clean. The hydrofluoric acid wet clean is an effective method for removing the oxide as it does not etch the polysilicon. Removing the sacrificial layers leaves behind a polysilicon tip which may be used to puncture a cavity or reservoir in a layer of substrate.

Figure 7H:
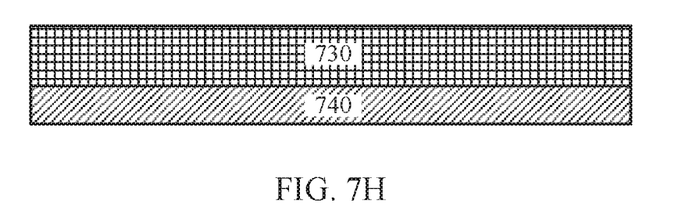

FIG. 7H depicts a layer of substrate 730 deposited on top of an etch stop layer 740. In one embodiment, the etch stop layer 740 corresponds to a top layer of material that remains unaltered by an etching process used to make a reservoir. In other (not pictured) embodiments, there may be multiple layers of substrate and multiple etch stop layers stacked.

Figure 7I:
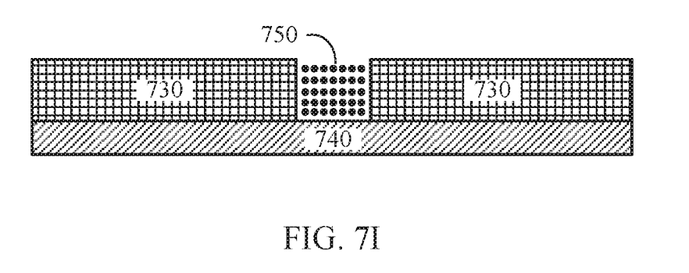
Figure 7J:
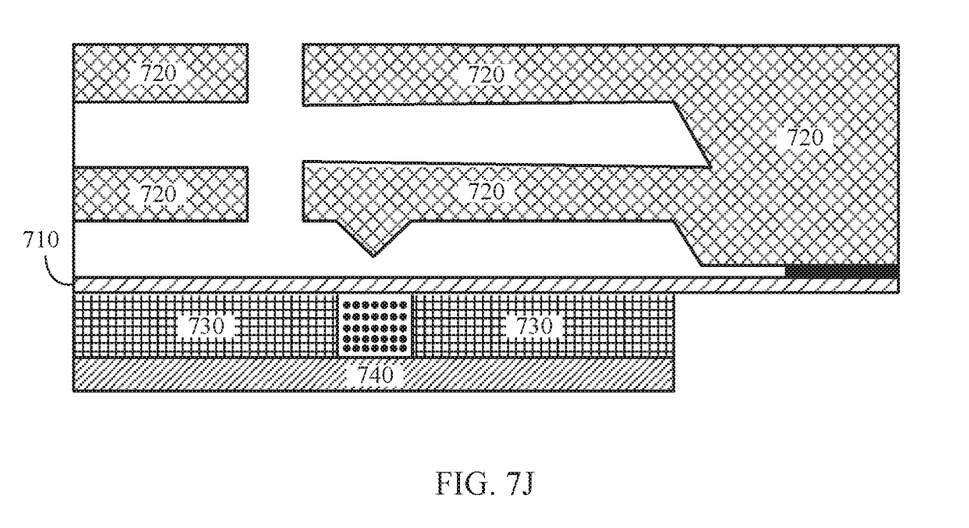

FIG. 7I depicts a reservoir 750 etched in a layer of substrate 730 and an etch stop layer 740. The reservoir may be produced by etching the layer of substrate 730. Similar to the step discussed with respect to FIG. 7B, a polymerizing reactive ion etch may be used to create reservoir 750 in substrate layer 730. As depicted with respect to FIG. 7I, a medication is deposited in reservoir 750. FIG. 7J depicts a polysilicon tip (fabricated according to the steps described in FIGS. 7A-7G) positioned over a substrate layer containing a reservoir 750 (fabricated according to the steps described in FIGS. 7H-7I).

Figure 7K:
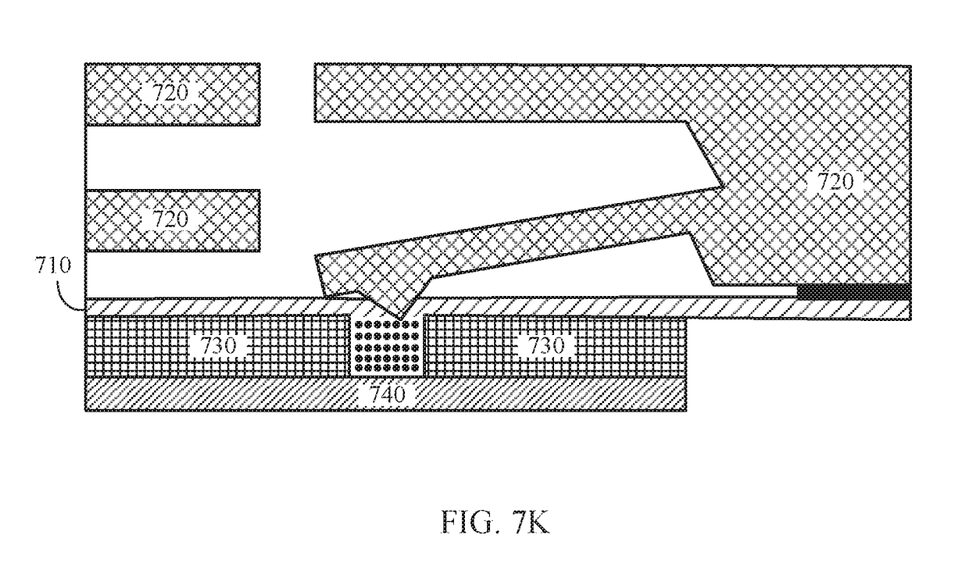
Figure 7L:
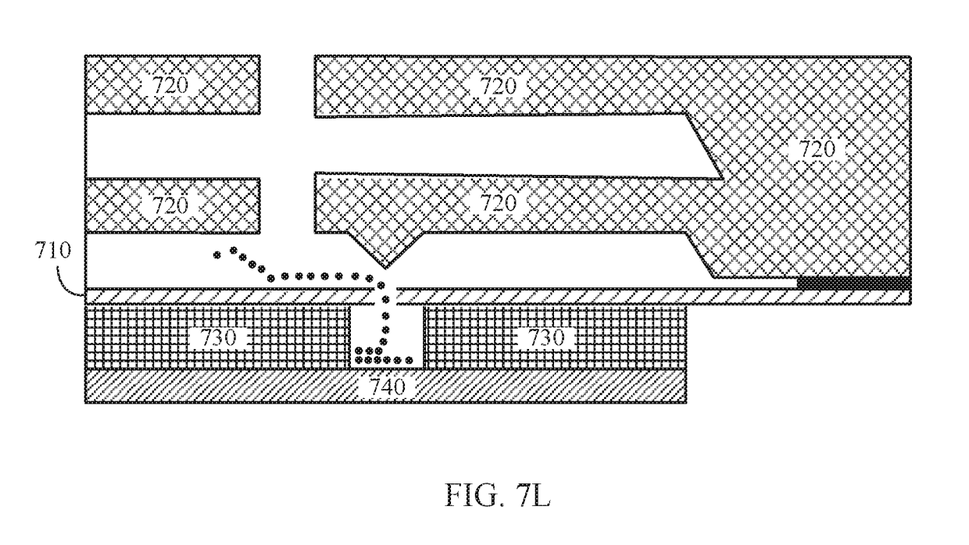

FIG. 7K depicts one example of a method for puncturing a sealing layer 710 with a polysilicon tip 720. With respect to the depicted embodiment, the polysilicon tip 720 is impelled forward by an applied electric field to puncture the sealing layer 710. As depicted, the polysilicon tip 720 is positioned in a manner such that when impelled forward, polysilicon tip 720 will puncture sealing layer 710 directly over reservoir 750. Reversing the applied electric field impels polysilicon tip 720 backwards, leaving a hole in reservoir 750. The hole in the reservoir 750 allows the stored medication to escape and flow out into the patient, as depicted with respect to FIG. 7L.

Figure 8:
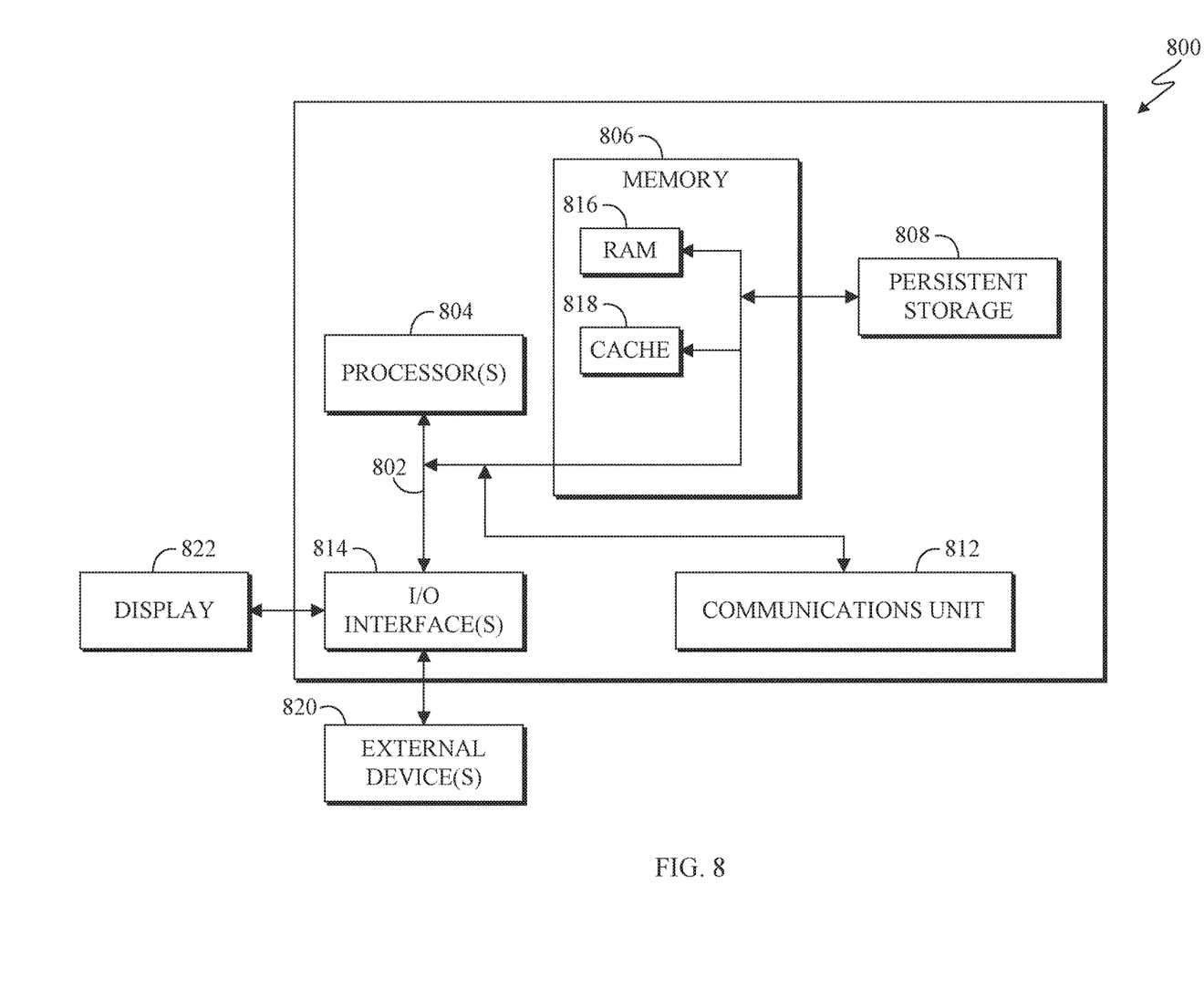
FIG. 8 depicts a block diagram of one example of a computer, in accordance with some embodiments of the present invention.

FIG. 8 depicts a block diagram of components of computer 800 in accordance with an illustrative embodiment of the present invention. It should be appreciated that FIG. 8 provides only an illustration of one implementation and does not imply any limitations with regard to the environments in which different embodiments may be implemented. Many modifications to the depicted environment may be made.

As depicted, the computer 800 includes communications fabric 802, which provides communications between computer processor(s) 804, memory 806, persistent storage 808, communications unit 812, and input/output (I/O) interface(s) 814. Communications fabric 802 can be implemented with any architecture designed for passing data and/or control information between processors (such as microprocessors, communications and network processors, etc.), system memory, peripheral devices, and any other hardware components within a system. For example, communications fabric 802 can be implemented with one or more buses.

Memory 806 and persistent storage 808 are computer-readable storage media. In this embodiment, memory 806 includes random access memory (RAM) 816 and cache memory 818. In general, memory 806 can include any suitable volatile or non-volatile computer-readable storage media.

One or more programs may be stored in persistent storage 808 for access and/or execution by one or more of the respective computer processors 804 via one or more memories of memory 806. In this embodiment, persistent storage 808 includes a magnetic hard disk drive. Alternatively, or in addition to a magnetic hard disk drive, persistent storage 808 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 808 may also be removable. For example, a removable hard drive may be used for persistent storage 808. Other examples include optical and magnetic disks, thumb drives, and smart cards that are inserted into a drive for transfer onto another computer-readable storage medium that is also part of persistent storage 808.

Communications unit 812, in these examples, provides for communications with other data processing systems or devices. In these examples, communications unit 812 includes one or more network interface cards. Communications unit 812 may provide communications through the use of either or both physical and wireless communications links.

I/O interface(s) 814 allows for input and output of data with other devices that may be connected to computer 800. For example, I/O interface 814 may provide a connection to external devices 820 such as a keyboard, keypad, a touch screen, and/or some other suitable input device. External devices 820 can also include portable computer-readable storage media such as, for example, thumb drives, portable optical or magnetic disks, and memory cards. Software and data used to practice embodiments of the present invention can be stored on such portable computer-readable storage media and can be loaded onto persistent storage 808 via I/O interface(s) 814. I/O interface(s) 814 also connect to a display 822.

Display 822 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computer/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computer/processing device receives computer readable program instructions from the network and forwards the computer readable program instructions for storage in a computer readable storage medium within the respective computer/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method comprising:
    assigning a public key to a medication delivery vehicle, wherein the public key is embedded in the medication delivery vehicle, and wherein the public key is an assigned identifier that is unique to an intended user;
    receiving, by one or more processors, an RFID signal containing a private key;
    determining, by one or more processors, whether the private key matches the public key embedded in the medication delivery vehicle;
    responsive to determining the private key matches the public key, moving, by one or more processors, a cantilevered beam toward a seal of a reservoir of the medication delivery vehicle, wherein the cantilevered beam is micromachined from a layer of material and coupled to the reservoir and comprises a sacrificial layer, wherein the sacrificial layer is removed thereby providing a tip for puncturing the seal;
    applying, by one or more processors, an electric field to the cantilevered beam that impels the tip forward and causes the tip to break through the seal of the reservoir; and
    changing, by one or more processors, the electric field to impel the micro-machined tip backward and thereby release a medication from the reservoir.

2. The method of claim 1, wherein the medication delivery vehicle further comprises a radiofrequency identification receptor.

3. The method of claim 2, wherein the electric field is applied responsive to receiving a radiofrequency identification signal.

4. The method of claim 1, wherein the medication delivery vehicle further comprises a chemical trigger sensor.

5. The method of claim 1, wherein changing the electric field comprises reversing the applied electric field to impel the micro-machined tip backward.

6. The method of claim 1, wherein changing the electric field comprises removing the applied electric field to stop impelling the tip forward.

7. The method of claim 6, further comprising applying a different electric field to impel the tip backward.

8. A drug delivery system comprising:
one or more computer readable storage media and program instructions stored on the one or more computer readable storage media, the program instructions comprising instructions to:
assign a public key to a medication delivery vehicle, wherein the public key is embedded in the medication delivery vehicle, and wherein the public key is an assigned identifier that is unique to an intended user;
receive an RFID signal containing a private key;
determine whether the private key matches the public key embedded in the medication delivery vehicle;
responsive to determining the private key matches the public key, move a cantilevered beam toward a seal of a reservoir of the medication delivery vehicle, wherein the cantilevered beam is micromachined from a layer of material and coupled to the reservoir and comprises a sacrificial layer, wherein the sacrificial layer is removed thereby providing a tip for puncturing the seal;
apply an electric field to the cantilevered beam that impels the tip forward and causes the tip to break through the seal of the reservoir; and
change the electric field to impel the micro-machined tip backward and thereby release a medication from the reservoir.

9. The computer program product of claim 8, wherein the medication delivery vehicle further comprises a radiofrequency identification receptor.

10. The computer program product of claim 9, wherein the electric field is applied responsive to receiving a radiofrequency identification signal.

11. The computer program product of claim 8, wherein the medication delivery vehicle further comprises a chemical trigger sensor.

12. The computer program product of claim 8, wherein instructions to change the electric field comprises instructions to reverse the applied electric field to impel the micro-machined tip backward.

13. The computer program product of claim 8, wherein instructions to change the electric field comprise instructions to remove the applied electric field to stop impelling the tip forward.

14. The computer program product of claim 13, further comprising instructions to apply a different electric field to impel the tip backward.

15. A drug delivery system comprising:
one or more computer processors;
one or more computer-readable storage media;
program instructions stored on the computer-readable storage media for execution by at least one of the one or more processors, the program instructions comprising instructions to:
assign a public key to a medication delivery vehicle, wherein the public key is embedded in the medication delivery vehicle, and wherein the public key is an assigned identifier that is unique to an intended user;
receive an RFID signal containing a private key;
determine whether the private key matches the public key embedded in the medication delivery vehicle;
responsive to determining the private key matches the public key, move a cantilevered beam toward a seal of a reservoir of the medication delivery vehicle, wherein the cantilevered beam is micromachined from a layer of material and coupled to the reservoir and comprises a sacrificial layer, wherein the sacrificial layer is removed thereby providing a tip for puncturing the seal;
apply an electric field to the cantilevered beam that impels the tip forward and causes the tip to break through the seal of the reservoir; and
change the electric field to impel the micro-machined tip backward and thereby release a medication from the reservoir.

16. The computer system of claim 15, wherein the medication delivery vehicle further comprises a radiofrequency identification receptor.

17. The computer system of claim 16, wherein the electric field is applied responsive to receiving a radiofrequency identification signal.

18. The computer system of claim 15, wherein instructions to change the electric field comprises instructions to reverse the applied electric field to impel the micro-machined tip backward.

19. The computer system of claim 15, wherein instructions to change the electric field comprise instructions to remove the applied electric field to stop impelling the tip forward.

20. The computer system of claim 19, further comprising instructions to apply a different electric field to impel the tip backward.

* * * * *